(12) United States Patent
Alexander (10) Patent No.: US 8,926,660 B2
(45) Date of Patent: Jan. 6, 2015

(54) SYSTEMS AND METHODS OF ANCHORING SURGICAL WIRES, CATHETERS, AND OTHER MEDICAL OBJECTS

(75) Inventor: Anthony Alexander, Seymour, IN (US)

(73) Assignee: Anthony Alexander, Seymour, IN (US)

( * ) Notice: Subject to any disclaimer, the term of this patent is extended or adjusted under 35 U.S.C. 154(b) by 1500 days.

(21) Appl. No.: 12/412,275

(22) Filed: Mar. 26, 2009

(65) Prior Publication Data

US 2009/0248028 A1  Oct. 1, 2009

Related U.S. Application Data

(60) Provisional application No. 61/039,689, filed on Mar. 26, 2008.

(51) Int. Cl.
| | |
|---|---|
| A61B 17/04 | (2006.01) |
| A61B 17/58 | (2006.01) |
| A61B 17/60 | (2006.01) |
| A61F 2/00 | (2006.01) |
| A61M 25/02 | (2006.01) |
| A61M 5/32 | (2006.01) |
| A44B 1/04 | (2006.01) |
| A44B 11/25 | (2006.01) |
| A44B 17/00 | (2006.01) |
| A61B 17/00 | (2006.01) |

(52) U.S. Cl.
CPC ............ *A61B 17/0487* (2013.01); *A61M 25/02* (2013.01); *A61B 17/00491* (2013.01); *A61M 2025/028* (2013.01); *A61M 2025/0286* (2013.01)
USPC ........... 606/232; 606/103; 604/174; 24/135 R (58) Field of Classification Search
USPC ......... 606/158, 138, 103, 232, 300, 324, 328, 606/60, 233, 250, 272, 263, 276–278, 148; 604/177, 178, 179, 180; 206/363, 370; 24/135 R, 339, 536, 569; 403/396, 398; 439/781–783, 786; 248/74.1, 74.2, 248/68.1

See application file for complete search history.

(56) References Cited

U.S. PATENT DOCUMENTS

| | | | | |
|---|---|---|---|---|
| 4,764,131 | A * | 8/1988 | Beinhaur | 439/781 |
| 7,250,054 | B2 * | 7/2007 | Allen et al. | 606/74 |
| 2003/0083657 | A1 * | 5/2003 | Drewry et al. | 606/61 |
| 2006/0271045 | A1 * | 11/2006 | Hubbard et al. | 606/61 |
| 2007/0219556 | A1 * | 9/2007 | Altarac et al. | 606/64 |

* cited by examiner

*Primary Examiner* — Todd Manahan
*Assistant Examiner* — Charles A Lutzow, III
(74) *Attorney, Agent, or Firm* — Klemchuk Kubasta LLP; Kirby B. Drake (57) ABSTRACT

The present disclosure generally provides systems and methods of anchoring surgical wires, catheters, leads, and other medical objects in an effective, efficient, and cost-sensitive manner. In one embodiment, the present disclosure could include a system to secure a medical object. The system could include a body having a first inner arm, a second inner arm, and a first outer arm. The first inner arm and the first outer arm could include a pronged structure. The system could also include a crossbar having a bore to receive a screw. The crossbar could be disposed between opposing surfaces of the first inner arm and the second inner arm and could be coupled to sliding grooves disposed along the opposing surfaces. When the screw is in an engaged position relative to the crossbar, the pronged structure could be configured to secure the medical object.

15 Claims, 5 Drawing Sheets

SYSTEMS AND METHODS OF ANCHORING SURGICAL WIRES, CATHETERS, AND OTHER MEDICAL OBJECTS

CROSS REFERENCE TO RELATED APPLICATION

This application claims benefit under 35 U.S.C. §119(e) of U.S. Provisional Patent Application No. 61/039,689 filed on Mar. 26, 2008 in the United States Patent and Trademark Office entitled "Reversible Tieless Surgical Anchor." The entire disclosure of U.S. Provisional Patent Application No. 61/039,689 is incorporated by reference as if fully disclosed herein.

TECHNICAL FIELD

The present disclosure generally relates to medical devices and, in particular, to systems and methods of anchoring surgical wires, catheters, leads, and other medical objects.

BACKGROUND

Conventional anchoring systems used in medical procedures generally lack proper stabilizing structure and compromise the integrity of the surgical wire, catheter, or other medical related object used in conjunction with the anchoring system. In addition, conventional anchoring systems typically fail to prevent translational movement of the wire, catheter, or other medical related object while the anchoring system is in an engaged position. Moreover, conventional anchoring systems typically fail to provide a reliable and secure system that maintains the integrity and relative position of the surgical wire, catheter, or other medical related object over time and that accommodates a patient's body movements.

SUMMARY

Embodiments of the present disclosure generally provide systems and methods of anchoring surgical wires, catheters, leads, and other medical objects.

In one embodiment, the present disclosure could provide an anchoring system. The anchoring system could include a body having a first inner arm and a second inner arm. The anchoring system could also include a crossbar having a bore to receive a screw. The crossbar could be disposed between opposing surfaces of the first inner arm and the second inner arm. The crossbar could also be coupled to sliding grooves disposed along the opposing surfaces. When the screw is in an engaged position, the anchoring system could secure a medical object with a pronged structure.

In one embodiment, the present disclosure could provide a method of anchoring a medical object. The method could include securing a suture to an anchor having a first inner arm, a second inner arm, and a crossbar. The crossbar could include a bore to receive a screw. The method could also include engaging the screw to wedge the crossbar against the first inner arm to secure a medical object disposed between the first inner arm and a second inner arm associated with the anchor.

In one embodiment, the present disclosure could include a system to secure a medical object. The system could include a body having a first inner arm, a second inner arm, and a first outer arm. The first inner arm and the first outer arm could include a pronged structure. The system could also include a crossbar having a bore to receive a screw. The crossbar could be disposed between opposing surfaces of the first inner arm and the second inner arm and could be coupled to sliding grooves disposed along the opposing surfaces. When the screw is in an engaged position relative to the crossbar, the pronged structure could be configured to secure the medical object.

Other technical features may be readily apparent to one skilled in the art from the following figures, descriptions and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

The present disclosure generally provides systems and methods of anchoring surgical wires, catheters, leads, and other medical objects in an effective, efficient, and cost-sensitive manner.

Figure 1:
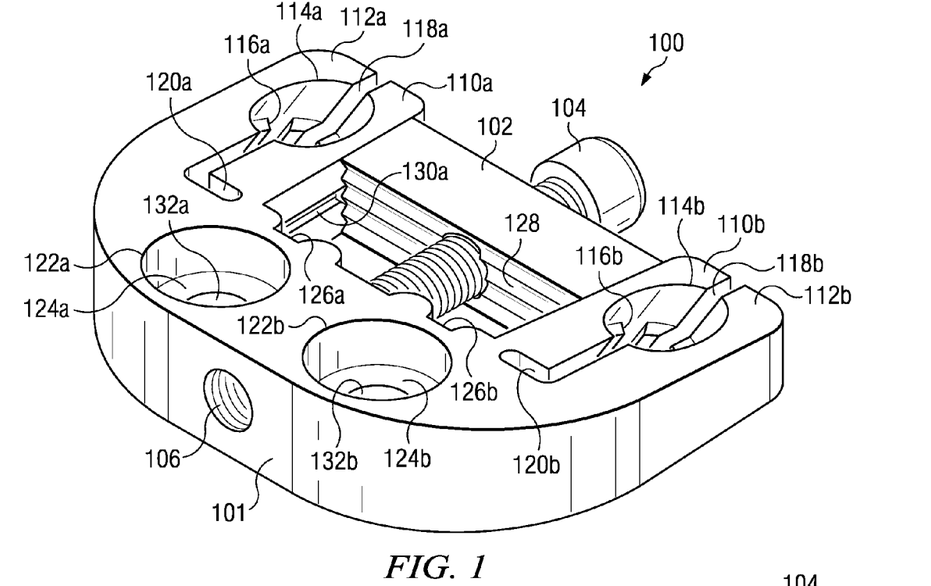
FIG. 1 is a perspective view of a system used to anchor surgical wires, catheters, leads, and other medical objects according to one embodiment of the present disclosure.
Figure 2:
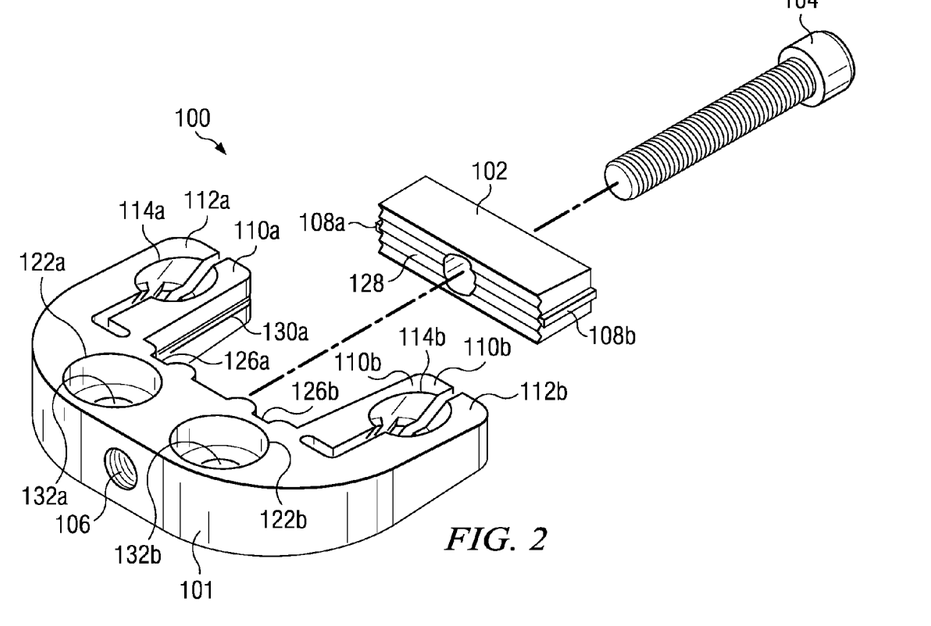
FIG. 2 is an exemplary exploded view of the system shown in FIG. 1.
Figure 3:
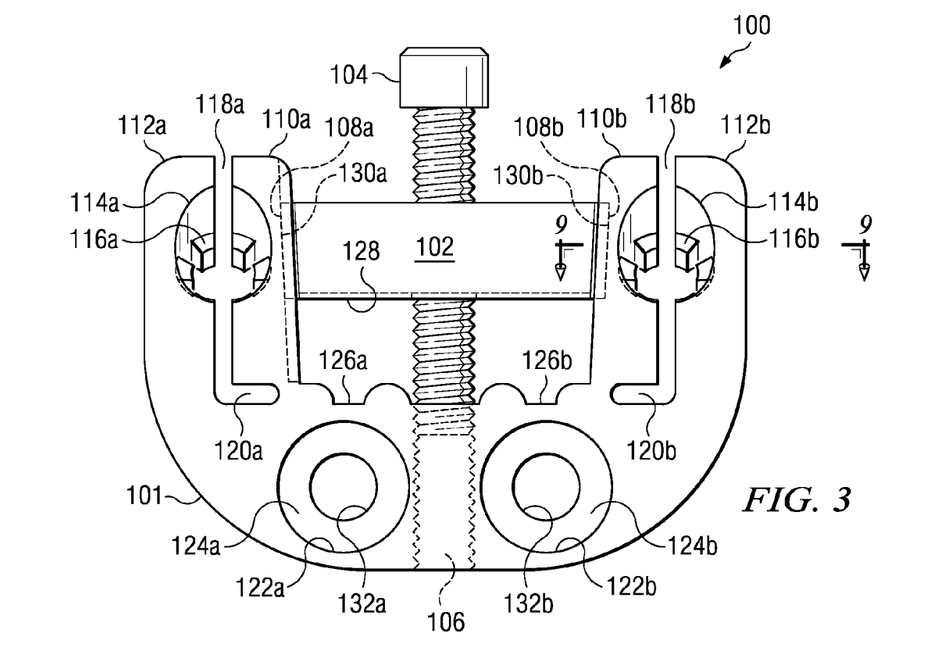
FIG. 3 is an exemplary top plan view of the system shown in FIG. 1.
Figure 4:
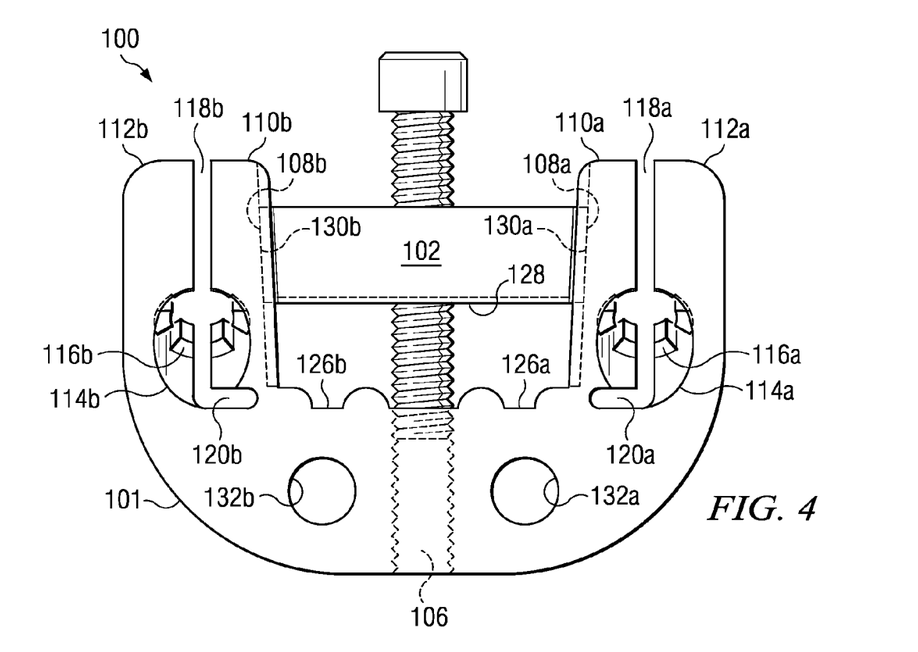
FIG. 4 is an exemplary bottom plan view of the system shown in FIG. 1.

FIG. 1 is a perspective view of system 100 used to anchor surgical wires, catheters, leads, sutures, ligaments, and other medical objects according to one embodiment of the present disclosure. FIG. 2 is an exemplary exploded view of system 100 shown in FIG. 1. FIGS. 3 and 4 are top and bottom plan view, respectively, of system 100 shown in FIG. 1. It should be understood that system 100 shown in FIGS. 1, 2, 3, and 4 are for illustrative purposes only and that any other suitable system or subsystem could be used in conjunction with or in lieu of system 100 according to one embodiment of the present disclosure.

Figure 5:
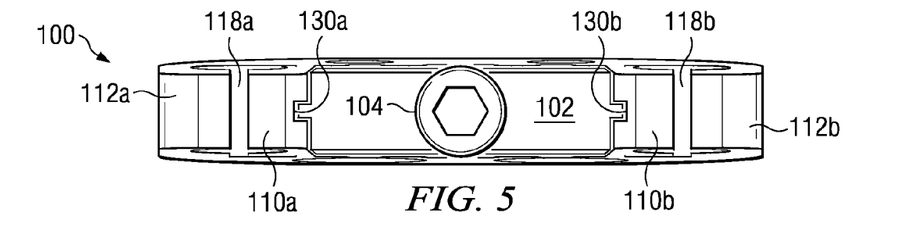
FIG. 5 is an exemplary top side view of the system shown in FIG. 1.
Figure 6:
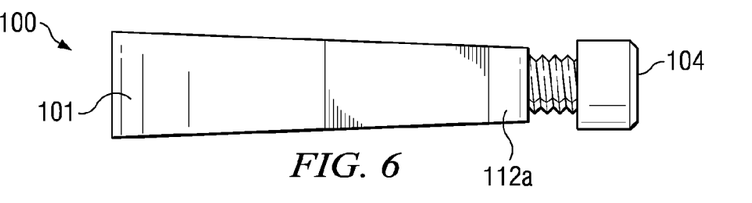
FIG. 6 is an another exemplary side plan view of the system shown in FIG. 1.
Figure 7:
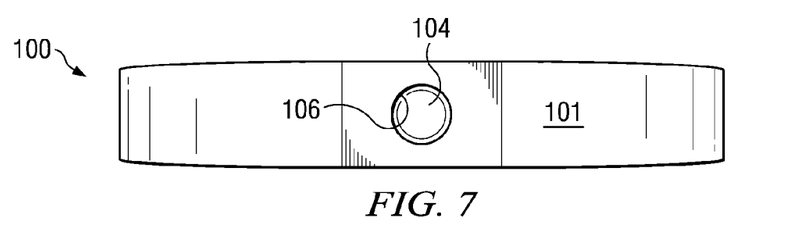
FIG. 7 is an exemplary bottom side view of the system shown in FIG. 1.
Figure 9:
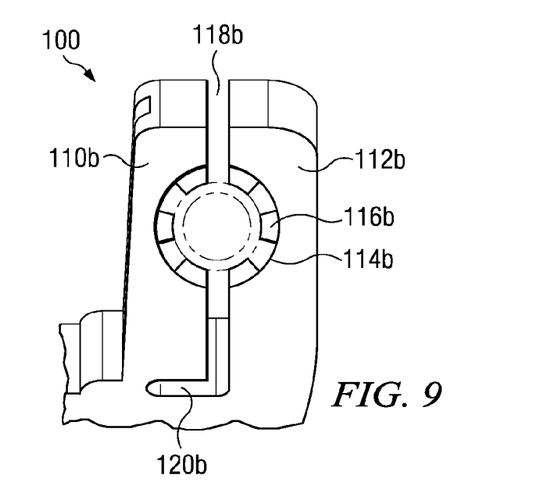
FIG. 9 is an exemplary view of an inner arm, outer arm, and pronged structure for the system shown from the perspective of reference 9-9 shown in FIG. 3.

Similarly, FIGS. 5, 6, and 7 various exemplary views of system 100 shown in FIG. 1. FIG. 5 is an exemplary top side view of system 100, while FIG. 6 is an exemplary side view of system 100 and FIG. 7 is an exemplary bottom side view of system 100. FIG. 9 is an exemplary view of an inner arm, outer arm, and pronged structure for system 100 shown from the perspective of reference 9-9 shown in FIG. 3. It should be understood that FIGS. 5-7 and 9 are for illustrative purposes only and that any other suitable system or subsystem could be used in conjunction with or in lieu of system 100 according to one embodiment of the present disclosure.

System 100 could be a reversible tieless surgical anchor to securely position and anchor one or more medical objects according to one embodiment of the present disclosure. In one embodiment, system 100 could securely position and anchor a medical object such as surgical wires, catheters, leads, sutures, ligaments, and other tube-like or wire-like objects without compromising the integrity of such objects. For example, system 100 could be used to anchor leads or metal wires to provide electrical current to pace makers, cochlear implants, neurostimulator leads, other medical devices, or any combination thereof. In other examples, system 100 could be used to anchor catheters or other tubing used for fluid flow, delivery, transport, or drainage. In addition, system 100 could also provide an anchoring platform for sutures, medical ties, stents, and other similar securing objects. In one embodiment, system 100 could be made of any suitable material including, for example, titanium, stainless steel, metal, plastic, polymer, bio-compatible material, or any combination thereof.

In the embodiment shown in FIG. 1, for example, system 100 could be an anchoring system that could generally include U-shaped body 101 with a tapered profile as generally shown, for example, in FIG. 6. U-shaped body 101 could mate with crossbar 102 and screw 104 to secure crossbar 102 to U-shaped body 101. U-shaped body 101 preferably includes a smooth, rounded, or beveled outer surface or edge to help reduce, minimize, mitigate, or eliminate the possibility of bruising or otherwise compromising the integrity of surrounding tissues or any medical objects anchored by system 100. In addition, when in an engaged position, system 100 generally eliminates, reduces, or mitigates lateral, translational, rotational, or other movement of the medical object anchored with system 100.

Screw 104 could include male mating threads that fit with female mating threads in channel 106 of U-shaped body 101. Screw 104 could include any suitable screw including, for example, precision, torque, round, fillister, washer, pan, binding, truss, hex, hex washer, slotted, Phillips, square, one-way, thread cutting, other suitable types or configurations of screws, or any combination thereof. In one embodiment, screw 104, when mated with channel 106, could be in a particular position or generally disposed flush with the top surface of crossbar 102. Channel 106 could extend through U-shaped body 101 of system 100 and could further extend to a distal end of system 100 as shown, for example, in FIG. 7.

U-shaped body 101, crossbar 102, and screw 104 could be made of identical, similar, or different materials. In one embodiment, U-shaped body 101, crossbar 102, and screw 104 could be made of any suitable material including, for example, titanium, stainless steel, metal, plastic, polymer, bio-compatible material, or any combination thereof.

As screw 104 bears down and mates with crossbar 102, crossbar 102 could move along guide 130a while coupled with track-like sliding grooves 108a and 108b (collectively referred to herein as sliding grooves 108) as illustrated later in, for example, FIG. 2. In one embodiment, sliding grooves 108 are disposed on inner arms 110a and 110b (collectively referred to herein as inner arms 110). Inner arms 110 wedge closer to outer arms 112a and 112b (collectively referred to herein as outer arms 112), respectively, as screw 104 moves crossbar 102 within U-shaped body 101. In one embodiment, inner arms 110 are tapered to translate the movement of crossbar 102 along sliding grooves 108 into a gripping force between inner arms 110 and outer arms 112.

Accordingly, in one embodiment, as screw 104 continues to move crossbar 102, the gap between inner arms 110 and outer arms 112 decreases. In doing so, openings 114a and 114b (collectively referred to herein as openings 114) decrease in size as the ends of prongs 116a and 116b (collectively referred to herein as prongs 116), respectively, become closer together. As a result, anchor openings 118a and 118b (collectively referred to herein as anchor openings 118) also decrease in size.

It should be understood that openings 114 could be configured or situated in any suitable form or structure. In the embodiment shown in, for example, FIG. 1, openings 114 could be situated at about a 45-degree angle relative to the surface or cross plane of system 100. The angled structure of openings 114 aid in providing relative positioning for a medical object placed in openings 114. FIG. 9, for example, provides an illustration of opening 114 from the perspective of reference 9-9 shown in FIG. 1.

It should also be understood that prongs 116 could be disposed in any suitable manner relative to openings 114. It should further be understood that prongs 116 could be any suitable shape, size, or combination to retain or secure the catheter or other medical object. For example, although various figures illustrate that system 100 includes two sets of prongs 116, it should be understood that system 100 could include any number of suitable of prongs 116. As a particular example, system 100 could include only one of set of prongs 116 and thus system 100 could accommodate just one catheter or other similar object. In another example, system 100 could include just one of suture openings 122, instead of the two shown in FIG. 1. Thus, in one embodiment, system 100 could accommodate just one suture or other similar object. In still other examples, system 100 could include multiple set of prongs 116 such as, for example, three sets of prongs 116 to accommodate three catheters or other similar objects.

In one embodiment, the wedging action precipitated by crossbar 102 is aided by the "living hinge" configuration associated with notches 120a and 120b (collectively referred to herein as notches 120). As described in detail later herein, should a catheter, for example, be placed in openings 114a and 114b while screw 104 is screwed into crossbar 102, inner arms 108 wedges closer to outer arms 112 and prongs 116 grasp the outer surface of the catheter. Thus, in one embodiment, the position and security of the catheter could be related to the relative positions of screw 104, crossbar 102, inner arms 108, outer arms 112, and prongs 116.

As also described in detail later herein, should a suture, for example, be placed in suture openings 122a and 122b (collectively referred to herein as suture openings 122) disposed along flanges 124a and 124b (collectively referred to herein as flanges 124) and apertures 132a and 132b (collectively referred to herein as apertures 132), respectively, the sutures could be secured in place using an number of different methods according to one embodiment of the present disclosure.

In addition, although suture openings 122 are illustrated as generally circular structures, it should be understood that suture openings 122 could include any suitable shape and size. In addition, although suture openings 122 are described herein as "suture openings," suture openings 122 could be used to secure any suitable object such as, for example, a tie, anchoring system, retaining apparatus, securing mechanism, medical object, other suitable system, or any combination thereof.

In one embodiment, a suture could be placed in suture opening 122a and disposed along flange 124a, one end of the suture could be secured in place by a rigid plug, elastic plug, adhesive, glue, metal stamp, other suitable securing or retaining system or method, or any combination thereof. The suture could also be secured in place by grooves 126a and 126b (collectively referred to as grooves 126) and grooves 128 under crossbar 102. Grooves 126 and grooves 128 could include any number, size, shape, or configuration of grooves, gripping objects, any suitable friction-causing or gripping surfaces, or any combination thereof in accordance with one embodiment of the present disclosure.

In one embodiment, once the suture is positioned relatively to, for example, surrounding tissue, one end of the suture could be stitched to the surrounding tissue using, for example, a "simple mattress" stitch, a stitch pattern similar to a "simple mattress" stitch, a single stitch, a double stitch, any other suitable stitch or stitch pattern, or any combination thereof. The same end could then be threaded through system 100 along groove 126a, as shown in, for example, FIGS. 8 and 10. While suture 804a is pulled taught and held in this temporarily position, the catheter or other medical object, for example, could be placed in openings 114a and 114b while screw 104 is screwed into crossbar 102, inner arms 108 wedges closer to outer arms 112 and prongs 116 grasp the outer surface of the catheter. Thus, in one embodiment, system 100 and the catheter are anchored securely and precisely positioned as desired.

System 100 therefore generally provides a system of anchoring surgical wires, catheters, leads, and other medical objects in an effective, efficient, and cost-sensitive manner. In addition, system 100 generally eliminates, reduces, or mitigates lateral, translational, rotational, or other movement of a medical object associated with system 100.

In one embodiment, system 100 could accommodate precision placement of, for example, sutures, ligaments, catheters, other flow systems, other medical objects, and any combination thereof. In addition, in one embodiment, system 100 could provide an anchoring system that allows absorption of energy created by, for example, any installed prosthetic, catheter, electrical, electromechanical, or any other device having any combination of devices thereof.

Figure 8:
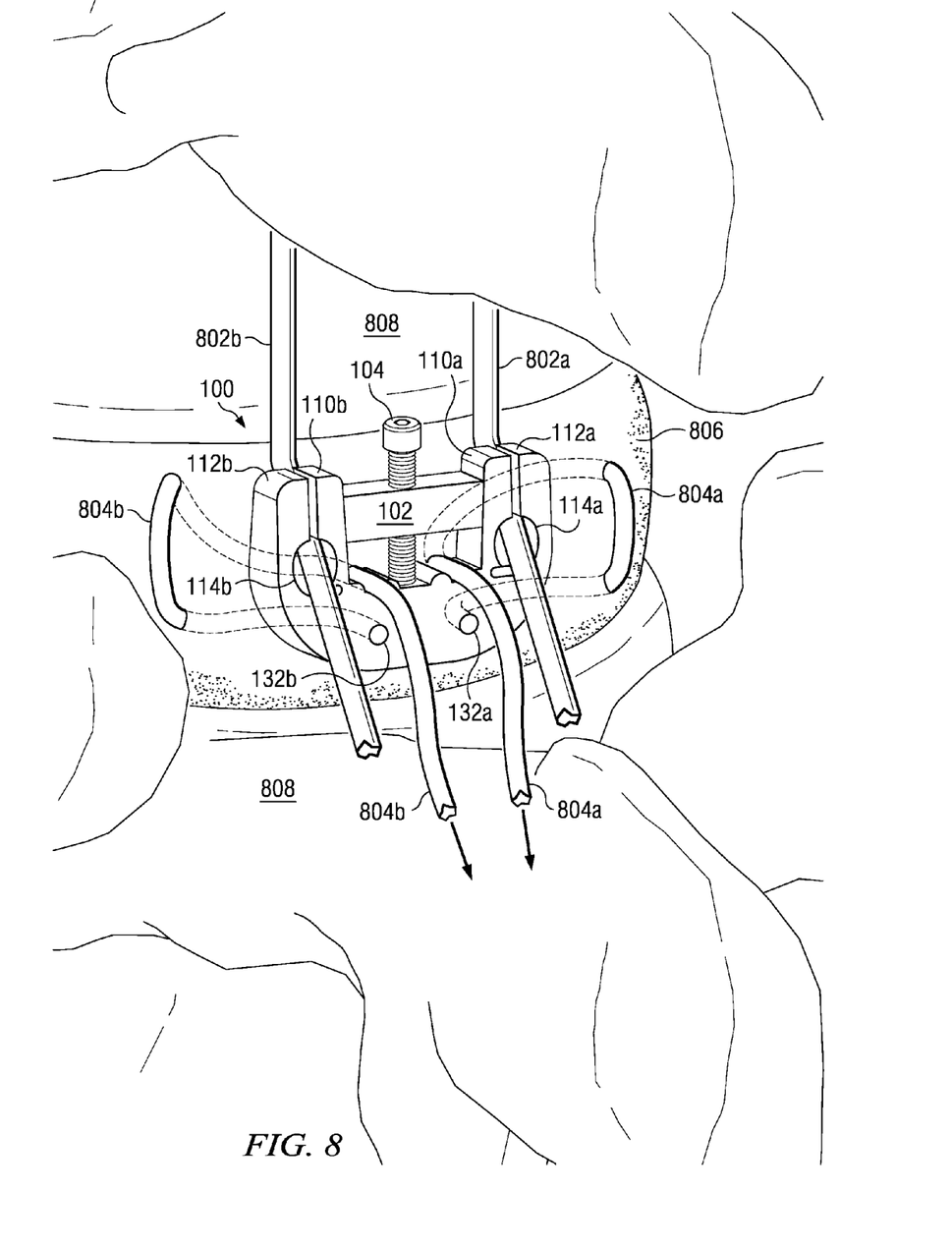
FIG. 8 is an exemplary perspective view of an example application for the system shown in FIG. 1.

FIG. 8 is an exemplary application for system 100 shown in FIG. 1. It should be understood that the application shown in FIG. 8 is for illustrative purposes only and that any other suitable application or sub-application could be used in conjunction with or in lieu of the application shown and described herein according to one embodiment of the present disclosure.

The exemplary application could generally include the use of system 100 as an anchoring system to anchor or otherwise secure or retain, for example, surgical wires, catheters, leads, or other medical objects in or about any tissue or other structure of the body according to one embodiment of the present disclosure. For example, in one embodiment, the application could include the use of system 100 (or method 1100 described later herein in conjunction with FIG. 11) to securely position or anchor a medical object such as surgical wires, catheters, leads, and other tube-like or wire-like objects without compromising the integrity of such objects to facilitate, for example, fluid flow, delivery, transport, or drainage.

As shown in FIG. 8, application 800 could include catheters 802a and 802b (sometimes collectively referred to herein as catheters 802), sutures 804a and 804b (sometimes collectively referred to herein as sutures 804), surrounding tissue 806, and spine 808 according to one embodiment of the present disclosure. Accordingly, in one embodiment, the application could include providing an anchoring system for catheters 802 relative to certain surrounding tissue 806 proximate to spine 808.

In one embodiment, sutures 804 secured to suture openings 122 on one end, while the second end is generally stitched to surrounding tissue 806 using, for example, a "simple mattress" stitch, a stitch pattern similar to a "simple mattress" stitch, a single stitch, a double stitch, other suitable stitch or stitch pattern, or any combination thereof.

Although the application shown in FIG. 8 illustrates an anchoring system for catheters 802, it should be understood that the application could also be used in a variety of other applications such as, for example, to anchor leads or metal wires to provide electrical current to pace makers, cochlear implants, neurostimulator leads, other medical devices, or any combination thereof.

Figure 10:
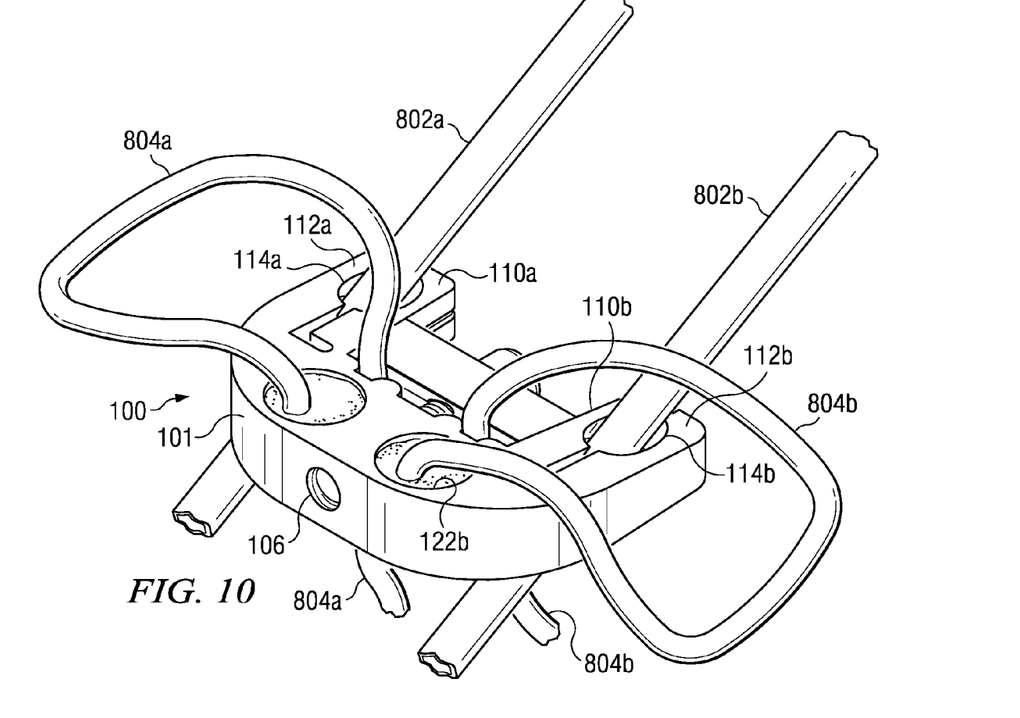
FIG. 10 is an exemplary illustration of catheters and sutures generally positioned in an engaged manner relative to the system shown in FIG. 1.

Now referring to FIG. 10, FIG. 10 is an exemplary illustration of catheters 802 and sutures 804 generally positioned in an engaged manner relative to system 100 shown in FIG. 1. It should be understood that the illustration shown in FIG. 10 is for illustrative purposes only and that any other suitable structure or sub-structure, or position or relative position of the elements, could be used or otherwise implemented in conjunction with or in lieu of according to one embodiment of the present disclosure.

Although FIG. 10 illustrates system 100 in a generally engaged manner with catheters 802 and sutures 804, the surrounding tissues or supporting structures have not been illustrated in FIG. 10 for ease of illustration and description. It should be understood that system 100 generally requires stitching or other securing measures to surrounding tissues or support structures to function properly.

The exemplary application illustrated in FIG. 10 generally includes the use of system 100 as an anchoring system to anchor or otherwise secure or retain, for example, surgical wires, catheters, leads, or other medical objects in or about any tissue or other structure of the body (not shown in FIG. 10) according to one embodiment of the present disclosure. For example, in one embodiment, the application could include the use of system 100 (or method 1100 described later herein in conjunction with FIG. 11) to securely position or anchor a medical object such as surgical wires, catheters, leads, and other tube-like or wire-like objects without compromising the integrity of such objects to facilitate, for example, fluid flow, delivery, transport, or drainage.

As shown in FIG. 10, sutures 804 could be secured in place and disposed in suture openings 122 (and along flanges 124—not shown in FIG. 10) according to one embodiment of the present disclosure. Sutures 804 could be secured in place using a number of different methods. For example, sutures 804 could be secured in place by a rigid plug, elastic plug, adhesive, glue, metal stamp, other suitable securing or retaining system or method, or any combination thereof. Similar descriptions could apply to sutures 804. It should be understood, that although suture openings 122 are illustrated as generally circular structures, suture openings 122 could include any suitable shape, size, or configuration and are not limited to the illustration shown in FIG. 10.

In one embodiment, sutures 804 are secured to suture openings 122 on one end, while the second end is generally stitched to surrounding tissue or other structure (not shown in FIG. 10) using, for example, a "simple mattress" stitch, a stitch pattern similar to a "simple mattress" stitch, a single stitch, a double stitch, any other suitable stitch or stitch pattern, or any combination thereof.

The respective second ends of sutures 804 could then be threaded through system 100 along groove 126a, as shown in, for example, FIG. 10. While sutures 804 are pulled taught and held in this temporary position, catheters 802 or other medical object, for example, could be placed in openings 114a and 114b. Screw 104 could then screw into crossbar 102, inner arms 108 wedges closer to outer arms 112 and prongs 116 grasp the outer surface of catheters 802. Thus, in one embodiment, catheters 802 are anchored securely and precisely positioned as desired.

Figure 11:
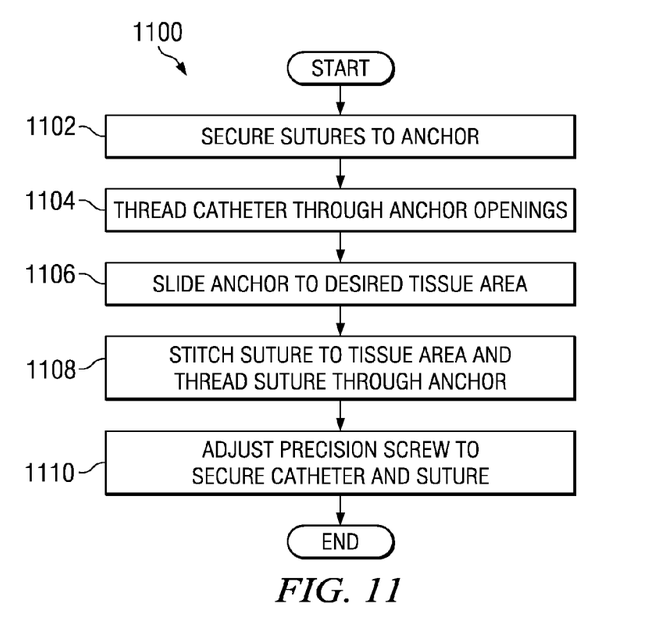
FIG. 11 is an exemplary method of using the system shown in FIG. 1 according to one embodiment of the present disclosure.

Now referring to FIG. 11, FIG. 11 is an exemplary method 1100 of using system 100 shown in FIG. 1 according to one embodiment of the present disclosure. It should be understood that FIG. 11 is for illustrative purposes only and that any other suitable method or sub-method could be used in conjunction with or in lieu of method 1100 according to one embodiment of the present disclosure. It should also be understood that the steps shown for method 1100 could be performed in a variety of different sequences and is not limited to the sequence described herein. In addition, although method 1100 generally describes step associated with catheter 802a and suture 804a, it should be understood that method 1100 could include identical or similar steps for catheter 802b and suture 804b.

In one embodiment, step 1102 could include securing one or more sutures such as, for example, suture 804a shown in FIG. 8 to an anchor such as, for example, system 100 shown in FIG. 1. Suture 804a could be secured to system 100 by disposing suture 804a in suture opening 122a and along flange 124a as shown in FIGS. 1 and 10. Suture 804a could be secured in place using a number of different methods. For example, suture 804a could be secured in place by a rigid plug, elastic plug, adhesive, glue, metal stamp, other suitable securing or retaining system or method, or any combination thereof according to one embodiment of the present disclosure.

In step 1104, method 1100 continues and could include threading a catheter, surgical wire, lead, or other tube-like or wire-like objects such as, for example, catheter 802a through suitable openings or apertures in system 100 such as, for example, opening 114a, and securing catheter 802a with a securing mechanism such as, for example, prongs 116 as shown in FIG. 8. In one embodiment, openings 114 could be configured to provide a 45-degree or so inclined or recessed channel relative to and through system 100. As such, catheter 802a could be disposed at an angle relative to system 100 as generally shown in, for example, FIGS. 8 and 10.

Once catheter 802a is in place, step 1106 could include repositioning system 100 to a particular area of catheter 802a relative to a desired tissue area or location. In one example, system 100 could be slidably moved along a surface of catheter 802a and proximate to a desired tissue area or structure.

In step 1108, a second end of suture 804a, which at this point has one end secured to suture opening 122a and flange 124a, is positioned and stitched into surrounding tissue such as for example tissue 806 shown in FIG. 8. In one embodiment, the second end of suture 804a could be stitched to surrounding tissue 806 using, for example, a "simple mattress" stitch, a stitch pattern similar to a "simple mattress" stitch, a single stitch, a double stitch, any other suitable stitch or stitch pattern, or any combination thereof. Step 1108 could also include threading suture 804a through system 100 and disposing suture 804a along groove 126a, as shown in, for example, FIGS. 8 and 10.

Accordingly, suture 804a could be pulled taught and held in this temporary position until the completion of step 1110. Alternatively, suture 804a could be threaded around a side surface of system 100, threaded or otherwise stitched into tissue 806, further threaded through the slot under crossbar 102 and along groove 126a, and held taught until completion of step 1110.

In step 1110, a screw such as, for example, screw 104 could be engaged with system 100 at crossbar 102 as shown in FIG. 1. Screw 104 could be screwed down until prongs 116 securely engage with catheter 802a as shown in, for example, FIGS. 8 and 10 according to one embodiment of the present disclosure. In addition, screw 104 could securely engage suture 804a with groove 126a and grooves 128 on the underside of crossbar 102 as shown in, for example, FIGS. 8 and 10.

Method 1100 therefore generally provides, for example, a method of anchoring catheters and sutures in a manner that helps reduce, minimize, mitigate, or eliminate the possibility of bruising or otherwise compromising the integrity of catheters 802, sutures 804, surrounding tissues 806, or any other medical objects anchored by or associated with system 100 according to one embodiment of the present disclosure.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An anchoring system comprising:
 a body with a tapered side profile, the body including a first inner arm, a first outer arm, a second inner arm, and a second outer arm;
 a crossbar detachably disposed between opposing surfaces of the first inner arm and the second inner arm and coupled to sliding grooves disposed along the opposing surfaces; and
 a screw,
 wherein the body and the crossbar have a channel to receive the screw so that as the screw mates with the crossbar, the crossbar moves along a guide to move the first inner arm toward the first outer arm and the second inner arm toward the second outer arm and prongs disposed between the first inner arm and the first outer arm grasp an outer surface of a first medical object to secure the first medical object without the crossbar contacting the first medical object.

2. The system of claim 1, further comprising a notch within the first inner arm forming a first hinge and a notch within the second inner arm forming a second hinge wherein the first hinge and the second hinge compress the prongs when subject to pressure from the crossbar.

3. The system of claim 1 further comprising:
 one or more openings disposed along flanges on the body to receive a suture.

4. The system of claim 3, wherein the crossbar comprises grooves to secure the suture.

5. The system of claim 4, wherein the body comprises secondary grooves to oppose the crossbar grooves.

6. The system of claim 1, wherein the medical object comprises at least one of:
a lead, a catheter, and a surgical wire.

7. The system of claim 1, wherein the first inner arm and the second inner arm are tapered.

8. The system of claim 1, wherein the first inner arm and the first outer arm comprise the prongs.

9. The system of claim 1 wherein prongs disposed between the second inner arm and the second outer arm grasp an outer surface of a second medical object to secure the second medical object without the crossbar contacting the second medical object.

10. A system to secure more than one medical object, the system comprising:
a body including a first inner arm having a first notch forming a first hinge within the first inner arm, a second inner arm having a second notch forming a second hinge within the second inner arm, a first outer arm, and a second outer arm; and
a crossbar detachably disposed between opposing surfaces of the first inner arm and the second inner arm and coupled to sliding grooves disposed along the opposing surfaces; and
a screw,
wherein the body and the crossbar have a bore to receive the screw so that when the screw mates with the crossbar, the first inner arm wedges toward the first outer arm and prongs disposed between the first inner arm and the first outer arm grasp an outer surface of a first medical object to secure the first medical object and the second inner arm wedges toward the second outer arm and prongs disposed between the second inner arm and the second outer arm grasp an outer surface of a second medical object to secure the second medical object, wherein the crossbar does not contact the first medical object or the second medical object.

11. The system of claim 10 further comprising:
a first opening and a second opening disposed on the body to each receive a suture.

12. The system of claim 11, wherein the crossbar comprises grooves to secure each suture.

13. The system of claim 12, wherein the body comprises secondary grooves to oppose the crossbar grooves.

14. The system of claim 10, wherein the medical object comprises at least one of:
a lead, a catheter, and a surgical wire.

15. The system of claim 10, wherein the first inner arm and the second inner arm are tapered.

* * * * *